United States Patent [19]

Reichenberger

[11] Patent Number: 4,664,111
[45] Date of Patent: May 12, 1987

[54] APPARATUS FOR PRODUCING TIME-STAGGERED SHOCK WAVES

[75] Inventor: Helmut Reichenberger, Eckental, Fed. Rep. of Germany

[73] Assignee: Siemens Aktiengesellschaft, Berlin and Munich, Fed. Rep. of Germany

[21] Appl. No.: 821,093

[22] Filed: Jan. 21, 1986

[30] Foreign Application Priority Data

Jan. 21, 1985 [DE] Fed. Rep. of Germany ....... 3501838

[51] Int. Cl.⁴ .............................................. A61B 17/22
[52] U.S. Cl. .................................... 128/328; 367/138
[58] Field of Search ...................... 128/328, 24 A, 660; 367/138, 151

[56] References Cited

U.S. PATENT DOCUMENTS 3,451,260  6/1969  Thurstone ............................. 73/67.9
4,526,168  7/1985  Hassler et al. .................... 128/328 X

FOREIGN PATENT DOCUMENTS 562266   10/1932  Fed. Rep. of Germany.
760163    5/1953  Fed. Rep. of Germany.
3312914  10/1984  Fed. Rep. of Germany.

Primary Examiner—Michael H. Thaler
Attorney, Agent, or Firm—Mark H. Jay

[57] ABSTRACT

A shock wave tube generates a plane shock wave which is divided into two partial waves by means of a splitting device, such as a cone. Adjacent the cone are first and second reflectors. The reflectors have different parabolic curvatures and different distances from the cone. Their respective foci coincide at a common point, where a concrement is located. The partial waves require different transit times to reach the common focus point. Time-staggered shock waves are obtained in the concrement with the use of a single shock wave tube.

7 Claims, 1 Drawing Figure

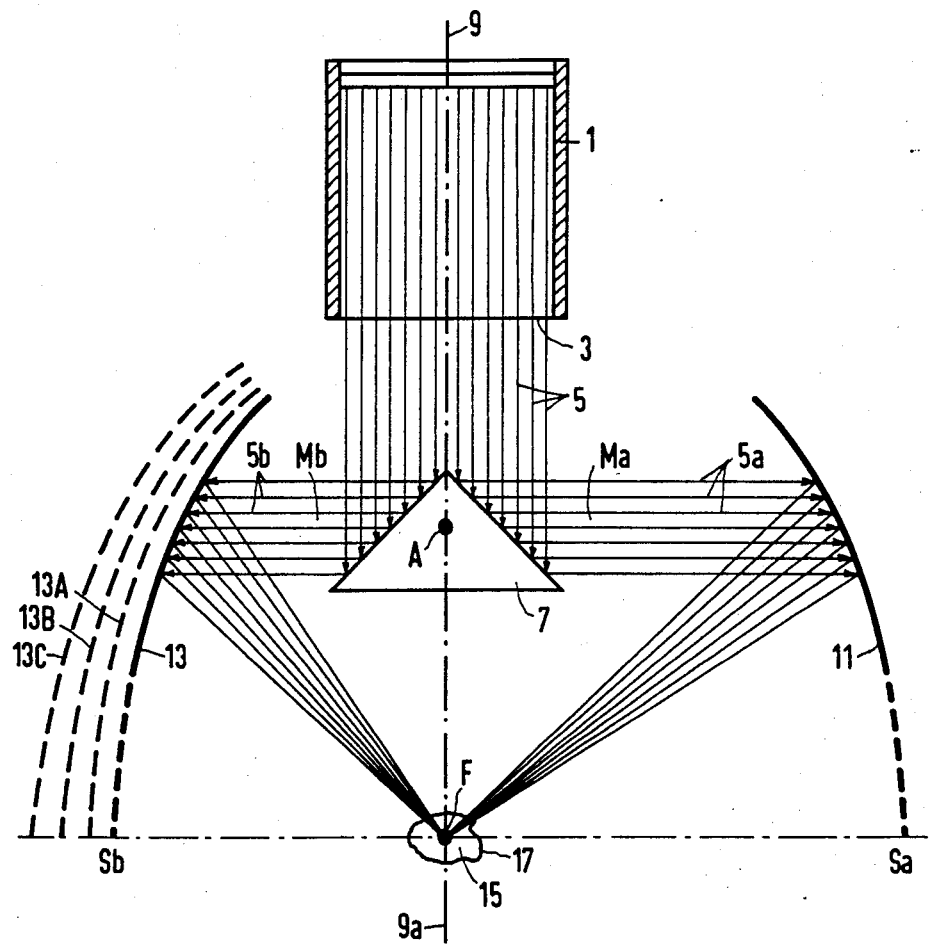

APPARATUS FOR PRODUCING TIME-STAGGERED SHOCK WAVES

BACKGROUND OF THE INVENTION

The invention relates to an apparatus for generating acoustic shock waves with a single shock wave tube and for focusing them onto a focus region. The invention particularly relates to the fragmentation of concrements (e.g. kidney stones) in a living being.

Shock wave tubes for generating acoustic shock waves are known. As indicated in German Offenlegungsschrift No. 33 12 014, shock wave tubes can be employed for the fragmentation of concrements in the body of a patient. This publication discloses a shock wave tube whose coil is curved, so that the emitted shock wave converges in a focus. In front of the coil, an insulating foil and a metal diaphragm are arranged. A voltage pulse is applied to the coil by means of a capacitor, and as a result the metal diaphragm is repelled from the coil. In this way the shock wave treatment is generated.

A shock-wave tube of the type considered herein is also described in commonly owned patent application Ser. No. 634,021, filed 07/24/1984 and entitled "Apparatus for the Contact-Free Desintegration of Calculi", the disclosure of which application is incorporated herein by reference.

Before the next shock wave is triggered, the capacitor must be recharged, which requires time.

For the fragmentation of, e.g. kidney stone in a adult person, a plurality (e.g. 500) of such shock waves (and hence a corresponding treatment time) is necessary. The effect of the shock waves can be improved if they are so closely spaced in time that they overlap in their action on the concrement. It has been proposed to provide several shock wave tubes in parallel and to activate them at short intervals in sequence. This procedure is relatively costly, because essential parts of the arrangement, such as the capacitor, spark gag and the shock wave tube itself, must be multiplied.

One object of the present invention is to develop an apparatus in which despite the existence of only one shock wave tube, time-staggered shock waves can be directed to the concrement.

SUMMARY OF THE INVENTION

In accordance with the invention, additional shock wave tubes are eliminated because the shock wave emitted by the single shock wave tube is split into a plurality of single, smaller secondary shock waves of lesser intensity. These secondary shock waves are caused to act on the concrement present in a focus region and are delayed relative to each other.

According to the invention, the shock wave tube generates a plane shock wave. A dividing device for the shock wave is provided. The dividing device splits the shock wave in the direction of a first and second reflector, and the first and second reflectors have a first and second focus, respectively. These foci are so arranged relative to the dividing device that they jointly lie in the focus region, and the first and second reflectors are at different distances from the dividing device.

If the appropriate dimensions are suitably chosen, two secondary shock waves can impinge on the concrement staggered in time in such a way that their actions overlap. At the same time, only one shock wave tube is required, so that the apparatus is compact and cost-effective.

A further advantage results if a plurality of differently shaped first or second reflectors are available and are detachably secured to the apparatus. By changing one reflector with another one, the magnitude of the time between the two successive shock waves in the concrement can then be adjusted. Such exchange may depend on the size or type of conrement to be destroyed.

BRIEF DESCRIPTION OF THE DRAWING

The single exemplary and non-limiting FIGURE schematically shows a preferred embodiment of the invention.

DETAILED DESCRIPTION OF PREFERRED EMBODIMENTS

In the FIGURE, 1 generally indicates a shock wave tube of known type. At the exit window 3 of the tube 1, a shock wave 5 issues after activation. As a result of the design of the shock wave tube 1, the shock wave 5 is here a plane wave, which impinges on a dividing device 7. The dividing device 7 consists of a material which relects ultrasonic waves. It is a cone, preferably a 90° cone, preferably made of brass. The apex of the dividing device 7 points toward the shock wave tube 1. Other cone-shaped dividing devices 7 may be used. The shock wave tube axis 9 coincides with the axis of rotation $9a$ of the cone.

The dividing device 7 reflects the shock wave 5 at right angles, so that it diverges perpendicular to the shock wave tube axis 9, i.e. radially. The part $5a$ of the shock wave 5 reflected to the right in the FIGURE impinges on a first curved reflector 11. The part $5b$ of the shock wave 5 reflected to the left impinges on a second, differently curved reflector 13. The first reflector 11 and the second reflector 13 are positioned so that they are at unequal distances (Ma>Mb) from the cone 7 and at the same time have their respective foci at a common point F. At this point F is located a concrement 15 to be fragmented. Point F is thus the focus region of the illustrated apparatus. Instead of two semicircular reflectors 11, 13, four sector-shaped reflectors may be arranged, whose curvature or parabolic parameters are different or, in the case of opposite sectors, may be equal.

It can be seen from the FIGURE that the first and second reflectors 11, 13 are part of a ring which is formed by rotation of the arc of a first and second parabola, whose summits lie at Sa and Sb, respectively, and whose focus lies at F, about the axis of the cone 7, and that the two reflectors 11, 13 are located on opposite sides of the axis $9a$ of cone 7.

Due to the greater distance Ma of the first reflector 11 from cone 7 as compared to the distance Mb of the second reflector 13 from cone 7, the right-hand parts $5a$ travels further to reach the common point F than does the left-hand part $5b$. This causes the right-hand part $5a$ to arrive at point F with a time delay relative to the left-hand part $5b$. This time delay should preferably be such that the right partial wave $5a$ arrives at the concrement 15 when the left partial wave $5b$ has already been reflected at the rear edge 17 of the concrement 15 and is in the process of returning through the concrement 15.

In the preferred embodiment, the distances Ma, Mb are referred to the center lines of the partial waves $5a$, $5b$. For a parabolic parameter of the first reflector 11 of e.g. $p_1 = 24$ cm and of the second reflector 13 of e.g. $p_2 = 21.5$ cm and a distance of the cone center A from point F of 10 cm, there results a path difference for the two partial waves 5a, 5b of about 1.5 cm. This difference corresponds to a time delay of about 10 microseconds and is well suited for achieving the superposition of the action of the two partial waves 5a and 5b.

To vary the time delay, a plurality of second reflectors 13, 13A, 13B, 13C may be made available, each having a different parabolic curvature. These second reflectors 13, 13A, 13B, 13C are then arranged each at a somewhat different distance Mo from the cone 7 in order to have their focus at the common point F. By exchanging second reflectors, there results a modified transit time of the partial wave 5b, whereby the time difference between the right partial wave 5a and the left partial wave 5b is adjustable. The reflectors 13, 13A, 13B, 13C not currently in use are removed.

Those skilled in the art will understand that changes can be made in the preferred embodiments here described, and that these embodiments can be used for other purposes. Such changes and uses are within the scope of the invention, which is limited only by the claims which follow.

What is claimed is:

1. Apparatus for producing time-staggered shock waves, comprising:
   means for producing a planar ultrasonic shock wave;
   ultrasonic beam splitting means for splitting said shock wave into at least two secondary ultrasonic shock waves; and
   reflecting means for focusing all said secondary shock waves upon a common focal region along paths of unequal lengths.

2. The apparatus of claim 1, wherein the beam splitting means comprises a cone of a material which reflects ultrasound.

3. The apparatus of claim 2 wherein said cone is a 90° cone with its apex pointing towards said producing means.

4. The apparatus of claim 2, wherein said cone is made of brass.

5. The apparatus of claim 1, wherein said reflecting means comprises first and second parabolic reflectors disposed on opposite sides of said beam splitting means.

6. The apparatus of claim 5, wherein a one of the parabolic reflectors is detachably secured to the apparatus and is replacable with another parabolic reflector of a different shape.

7. Apparatus for producing time-staggered shock waves, comprising:
   means for producing a planar ultrasonic shock wave;
   ultrasonic beam splitting means for splitting ultrasound shock waves into at least two secondary ultrasonic shock waves; and
   reflecting means for focusing all said secondary shock waves upon a common focal region along paths of unequal lengths, said reflecting means including means for adjusting the length of at least one of said paths.

* * * * *